United States Patent [19]
Salama

[11] Patent Number: 5,693,001
[45] Date of Patent: Dec. 2, 1997

[54] URINARY CONTROL WITH INFLATABLE SEAL AND METHOD OF USING SAME

[76] Inventor: Fouad A. Salama, 3220 Valley Ridge Ct., West Des Moines, Iowa 50265

[21] Appl. No.: 725,030

[22] Filed: Oct. 2, 1996

Related U.S. Application Data

[62] Division of Ser. No. 233,308, Apr. 26, 1994, Pat. No. 5,634,877, which is a division of Ser. No. 61,770, May 14, 1993, Pat. No. 5,306,226, which is a continuation of Ser. No. 600,629, Oct. 22, 1990, abandoned, which is a continuation-in-part of Ser. No. 307,992, Feb. 9, 1989, Pat. No. 4,968,294.

[51] Int. Cl.⁶ ............................................ A61F 2/02
[52] U.S. Cl. ........................... 600/290; 128/DIG. 25; 604/247
[58] Field of Search .................. 600/29–32; 604/34, 604/247; 128/830, 834, 842, 843, 885, 886, 887, DIG. 25; 251/342

[56] References Cited

U.S. PATENT DOCUMENTS

| | | | |
|---|---|---|---|
| 2,230,150 | 1/1941 | Winder | 604/96 |
| 2,547,758 | 4/1951 | Keeling | 604/174 |
| 2,690,595 | 10/1954 | Raiche | 604/96 |
| 3,394,705 | 7/1968 | Abramson | 604/280 |
| 3,459,175 | 8/1969 | Miller | 604/96 |
| 3,631,857 | 1/1972 | Maddison | 604/349 |
| 3,707,146 | 12/1972 | Cook et al. | 604/96 |
| 3,841,304 | 10/1974 | Jones | 128/DIG. 25 |
| 3,977,408 | 8/1976 | Mackew | |
| 4,089,337 | 5/1978 | Kronner | 604/178 |
| 4,211,233 | 7/1980 | Lin | 604/96 |
| 4,350,161 | 9/1982 | Davis, Jr. | |
| 4,419,097 | 12/1983 | Rowland | 604/352 |
| 4,432,757 | 2/1984 | Davis, Jr. | |
| 4,575,371 | 3/1986 | Nordquist et al. | 604/96 |
| 4,626,250 | 12/1986 | Schneider | 604/347 |
| 4,710,169 | 12/1987 | Christopher | 604/104 |
| 4,810,247 | 3/1989 | Glassman | 604/171 |
| 4,813,935 | 3/1989 | Haber et al. | 604/103 |
| 4,820,270 | 4/1989 | Hardcastle et al. | 604/96 |
| 4,946,449 | 8/1990 | Davis, Jr. | 128/DIG. 25 |
| 5,007,897 | 4/1991 | Kalb et al. | 604/96 |
| 5,030,199 | 7/1991 | Barwick et al. | 600/29 |

FOREIGN PATENT DOCUMENTS

| | | | |
|---|---|---|---|
| 2818119 | 11/1979 | Germany | 604/96 |
| 479468 | 3/1954 | Italy | 604/96 |

Primary Examiner—Michael Buiz
Assistant Examiner—Nancy Mulcare
Attorney, Agent, or Firm—Zarley, McKee, Thomte, Voorhees, & Sease

[57] ABSTRACT

A urine tube extends through a balloon which is inflatable in the neck of a bladder to form a seal around the urine tube. The balloon has a shape corresponding to the shape of the bladder chamber at the urethra orifice to facilitate establishing a seal. A valve is provided on the outlet end of the urine tube and an air tube extends along the substantial length of the urine tube into the balloon. A hypodermic syringe or the like may be inserted into the inlet end of the air tube for inflating the balloon. A hydrogel collar is positioned around the urine tube against the body at the outlet end of the urethra to hold the balloon in tight engagement with the bladder neck at the urethra orifice.

17 Claims, 2 Drawing Sheets

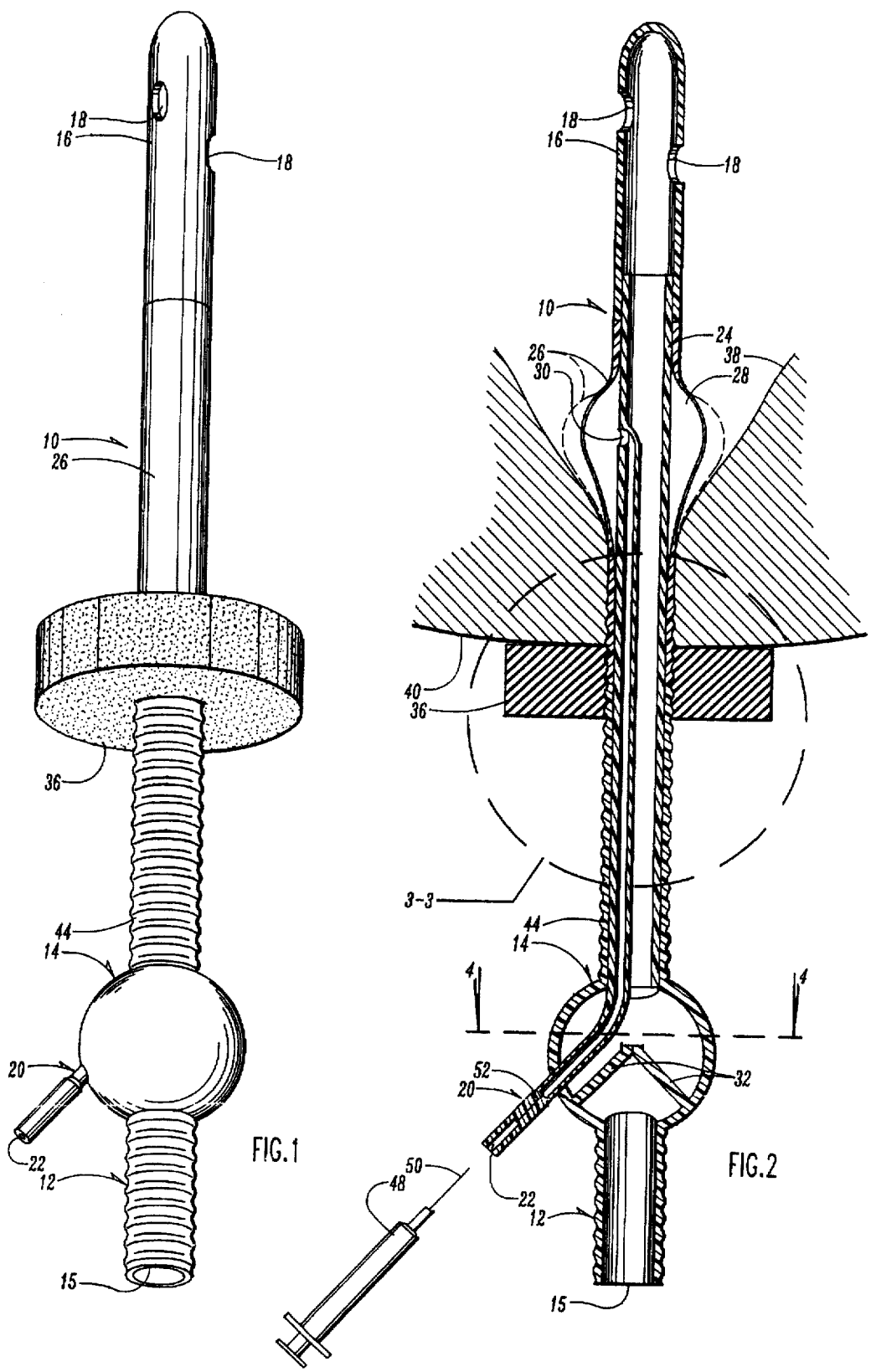

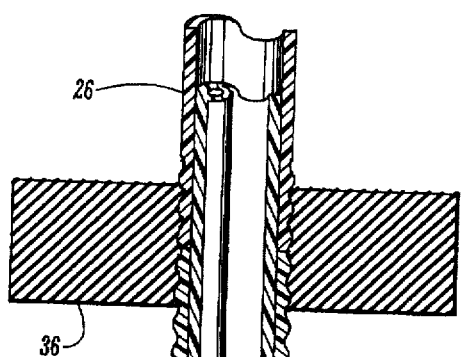
FIG.3
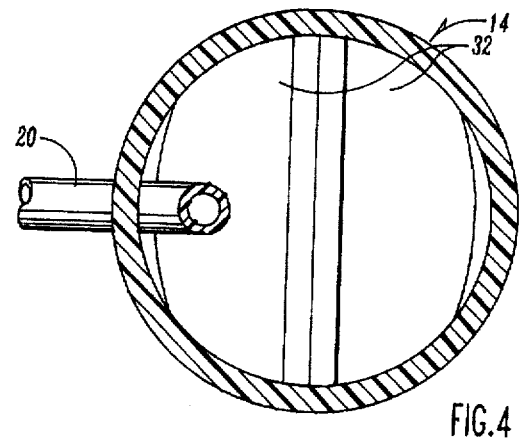
FIG.4
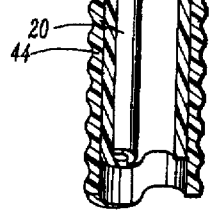
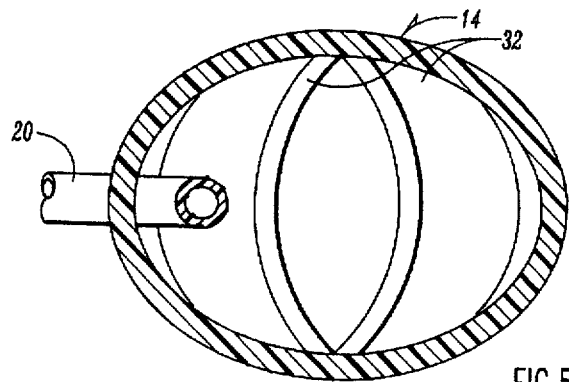
FIG.5
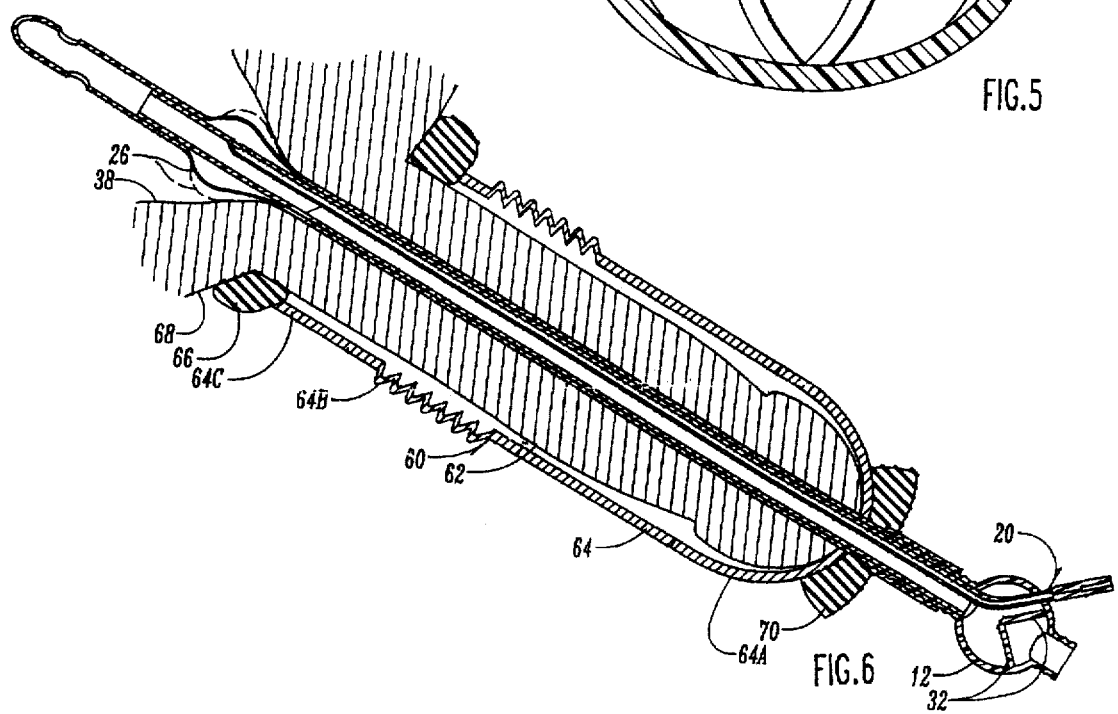
FIG.6

5,693,001

URINARY CONTROL WITH INFLATABLE SEAL AND METHOD OF USING SAME

This is a Divisional of application Ser. No. 08/233,308, filed Apr. 26, 1994, now U.S. Pat. No. 5,634,877, which is a divisional application of 08/061,770, filed on May 14, 1993 and issued as U.S. Pat. No. 5,306,226, on Apr. 26, 1994; which is a continuation of Ser. No. 07/600,629, filed Oct. 22, 1990 now abandoned; which is a continuation in part of Ser. No. 07/307,992, filed on Feb. 9, 1989, and issued as U.S. Pat. No. 4,968,294 on Nov. 6, 1990, URINARY CONTROL VALVE & METHOD OF USING SAME.

BACKGROUND OF THE INVENTION

Incontinence is a problem for many people including older adults. Present day approaches to dealing with incontinence such as the Foley catheter often times causes urinary tract infection. A bag for urine is required and smell becomes a problem. The chances of infection are increased each time the bag is changed. The cost for the Foley catheters and bags is substantial. An inflatable conventional spherical balloon is used to keep the catheter in the bladder, but leakage around the catheter occurs and is a problem. It was not an object of this product to provide a seal around the catheter at the bladder orifice.

In my co-pending application I have disclosed a urethral valve positioned in the orifice of the urethra. In some instances, leakage may occur around the outside of the valve. What is needed is a simple inexpensive device for controlling urine flow in the urethra which is compatible to the body and will not cause discomfort, infection and pass urine only through operation of the valve rather than around the outside of the catheter.

SUMMARY OF THE INVENTION

A urinary tube extends into the, urethra and continues into the bladder. An inflatable balloon having a lower end portion extending into the urethra has a shape corresponding to the shape of the inner wall surface of the bladder at the orifice, extends around the bladder end of the urinary tube and an air line extends through the urine tube to outside the urethra where it is adapted to be connected to an air pump for inflating the balloon to provide a plug seal in the urethra around the urinary tube in the neck and orifice of the bladder. A valve is provided in the urinary tube outside of the urethra.

An anchoring collar of hydrogel frictionally engages the exterior of the urinary tube and is positioned against the outer end of the urethra to hold the balloon lower in portion in tight sealing engagement in the urethra in the neck of the bladder.

The urinary control of this invention when used by a male includes the additional use of a support shell around the penis to stabilize the urinary tube which extends through the penis. The anchoring collar of hydrogel is positioned against the outer end of the support shell. The shell is one piece but includes a plurality of sections to allow for fitting the support shell to penises of different sizes. A collar of hydrogel is also placed between the inner end of the shell sections and the pubic bone base of the penis. An accordion type section is included to give the shell flexibility in accommodating penises of different lengths and to permit them to be disposed at varying angles to the body.

A hypodermic syringe or the like may function as an air pump when its needle is inserted into the air tube to inflate the balloon.

DESCRIPTION OF THE DRAWINGS

FIG. 1 is a fragmentary perspective view of the urinary control with inflatable seal.

FIG. 2 is a longitudinal cross-sectional view of the urinary control in the urethra of a female.

FIG. 3 is an enlarged cross-sectional view of the structure indicated by the line 3—3 in FIG. 2.

FIG. 4 is a cross-sectional view taken along line 4—4 in FIG. 2 showing the valve in a closed condition.

FIG. 5 is a view similar to FIG. 4 but showing the valve in an open condition.

FIG. 6 is a view similar to FIG. 2 but showing the urinary control in the urethra of a male.

DESCRIPTION OF THE PREFERRED EMBODIMENT

The urinary control of this invention is referred to generally by the reference numeral 10 as seen in FIG. 1 and includes a urine tube 12 in which a valve 14 is connected. The tube 12 has an outer outlet end 15 and an inner inlet end 16 with sidewall openings 18.

An air tube 20 extends into the valve body 14 and along the length of the tube 12 towards the inlet end 16. The air tube 20 has an inlet end 22 and an outlet end 24 positioned in a balloon 26 formed in part by the sidewalls of the urine tube 14. Balloon chamber 28 is provided. The air tube outlet end includes an opening 30 in chamber 28.

The valve body 14 includes a pair of oppositely disposed blade elements 32 normally closed. Pressure on the opposite sidewalls of the valve body 14 will cause the valve elements 32 to spread as seen in FIG. 5 and allow urine to flow toward the outlet end 14.

An anchoring collar means 36 of hydrogel is provided around the urine tube 12 outwardly of the balloon 26 and frictionally engages the outer surface of the urine tube 12 to hold the walls of the balloon 26 in tight sealing contact with the bladder orifice and neck 38 as seen in FIG. 2. The balloon 26 is shaped to correspond to the shape of the inner side walls of the bladder at the orifice to provide a seal around the catheter thereby preventing leakage. This shape is generally pear shape. As seen in FIGS. 2 and 6, the balloon 26 when inflated includes an enlarged upper portion which merges into a downwardly extending reduced in size lower portion. In the female, the collar 36 presses against the body around the opening to the urethra. A sleeve 42 also extends around the urine tube 12 and may be adjusted tightly against the collar 36 to assist in holding the collar tight against the person's body at the outlet end of the urethra. Rounded serrations 44 are provided along the outside of the urine tube 12 and register with serrations on the inside face of the collar 36 and serve to hold the collar 36 in place in turn holding the balloon seal 26 in place thereby preventing leakage around the tube 12.

A hypodermic syringe 48 functions as an air pump and has a needle 50 which is inserted into the inlet end 22 of the air tube 20. The inlet end 22 has a passageway 52 normally closed except when opened by the needle 50 thereby allowing air to be introduced into the tube to fill the balloon 26 but when the needle 50 is removed the passageway is sealed preventing air from escaping and deflating the balloon.

When the urinary control of this invention is used on a male, a one piece support shell 60 is provided around the penis 62 and includes an outer section 64 having an outer end 64A being rounded to the curvature of the head of the penis. An accordion pleats section 64B interconnects the outer section 64 with a base section 64C. The base section 64C presses against a hydrogel collar 66 which presses against the base (pubic bone) 68 of the penis. A second hydrogel collar 70 is positioned against the outer end of the rounded section 64A to hold the urine tube 12 in place such that the lower end portion of the balloon 26 when inflated is pressed against the bladder neck 38 and into the urethra. Among the properties of hydrogel is that it is soft and pliable but yet firm.

In use it is seen that the urine tube 12 will be inserted into the urethra of the male or female far enough that the lower end portion of the balloon 26 will function as a retention means and the lower portion will be seated in the urethra at the neck 38 of the bladder and functions as a plug to prevent urine flow on the outside of the urine tube 12. Air is introduced into the air tube 20 through the use of a hypodermic syringe. A hydrogel collar is then positioned against the body at the outer end of the urethra to hold the balloon 26 in position to maintain the seal in the urethra and the bladder neck 38. The balloon is inflated from the solid line position in FIG. 2 to the dash line inflated condition. When fully installed, no urine can leak around the urine tube 12 due to the seal the balloon 26 provides in the uretha and bladder neck 38. Urine can enter the openings 18 in the inlet end 16 of the urine tube 12 and pass into the valve 14 and upon actuation of the valve blades 32 by applying pressure to opposite sides of the valve 14, the valve will be open for drainage of the bladder through the outlet end 15.

The valve 14 and urine tube 12 are formed from elastomer silicone material of a 50 or 55 durometer from Dow Corning, Midland, Mich. Tubing of this material is flexible and longitudinally collapsible such that longitudinal compressive pressure applied to it will not unseat the balloon lower portion in the urethra at the neck and orifice of the bladder and cause leakage around the tubing. The balloon 26 may have a capacity of approximately 40 cc's.

I claim:

1. A urethral catheter for controlling a flow of urine from a bladder through a urethra of a person, said bladder having an interior, a neck region, and an orifice fluidly communicating with said urethra, said urethral catheter comprising:

a urine tube, said urine tube having an exterior;

an inflatable balloon, said inflatable balloon being connected to said urine tube, said inflatable balloon having an interior, said urine tube extending through said interior of said inflatable balloon and fluidly communicating with the interior of the bladder, said inflatable balloon having a generally non-spherical shape including an upper portion and a lower portion, said upper portion being generally larger than said lower portion, said lower portion of said inflatable balloon being sized so as to be received at least partially within the urethra generally proximate to the neck region and the orifice of the bladder to form a plug seal within the urethra when said inflatable balloon is inflated and said upper portion of said inflatable balloon is seated within the interior of the bladder contacting the bladder closely proximate to the neck region and the orifice, and whereby the plug seal formed by the inflatable balloon within the urethra prevents the flow of urine from within the bladder through the urethra on the exterior of the urine tube.

2. The urethral catheter of claim 1 wherein an anchoring member is operatively connected to the urine tube for maintaining the lower portion of said inflatable balloon closely adjacent to the neck and orifice of the bladder and within the urethra.

3. The urethral catheter of claim 1 wherein an anchoring member is connected to the urine tube for operative engagement with the body member adjacent to the distal end of the urethra to seat the downwardly depending lower end portion of the inflatable balloon closely adjacent to the neck and the orifice of the bladder and within the urethra.

4. The urethral catheter of claim 3 and a support shell for generally surrounding the penis, said support shell having a distal end and an inner surface, the outlet end of the urine tube extending outwardly beyond said distal end of said support shell with the anchoring member being in operative engagement with said distal end of said support shell, said inner surface of said support shell operatively engaging the penis generally proximate to the distal end thereof; and said anchoring member providing resistance when pulling the inflatable balloon downwardly for seating the inflatable balloon by pulling the inflatable balloon downwardly toward the neck and the orifice of the bladder.

5. The urethral catheter of claim 1 wherein the urine tube is a flexible, longitudinally collapsible urine tube such that longitudinal compressive pressure applied to the urine tube will not unseat the downwardly extending reduced-in-size portion of the inflatable balloon from within the urethra and cause leakage on the exterior of the inflation tube or the exterior of the urine tube.

6. The urethral catheter of claim 1 wherein the urine tube is fabricated from an elastomeric silicone material.

7. The urethral catheter of claim 1 wherein the inflatable balloon has a volume, said volume being generally less than or equal to 40 cc.

8. The urethral catheter of claim 1 wherein a collar encircles the urine tube and the inflation tube for being positioned in operative engagement with a person's pubic bone to thereby limit longitudinal movement of the urine tube and the inflation tube into the bladder.

9. The urethral catheter of claim 1 wherein the urine tube includes a valve for selectively preventing the flow of urine through the urine tube.

10. The urethral catheter of claim 9 wherein an anchoring member is operatively connected to the urine tube for maintaining the lower portion of said inflatable balloon closely adjacent to the neck and orifice of the bladder and within the urethra.

11. The urethral catheter of claim 9 wherein an anchoring member is connected to the urine tube for operative engagement with the body member adjacent to the distal end of the urethra to seat the downwardly depending lower end portion of the inflatable balloon closely adjacent to the neck and the orifice of the bladder and within the urethra.

12. The urethral catheter of claim 11 and a support shell for generally surrounding the penis, said support shell having a distal end and an inner surface, the outlet end of the urine tube extending outwardly beyond said distal end of said support shell with the anchoring member being in operative engagement with said distal end of said support shell, said inner surface of said support shell operatively engaging the penis generally proximate to the distal end thereof; and said anchoring member providing resistance when pulling the inflatable balloon downwardly for seating the inflatable balloon by pulling the inflatable balloon downwardly toward the neck and the orifice of the bladder.

13. The urethral catheter of claim 9 wherein the urine tube is a flexible, longitudinally collapsible urine tube such that longitudinal compressive pressure applied to the urine tube will not unseat the downwardly extending reduced-in-size portion of the inflatable balloon from within the urethra and cause leakage on the exterior of the inflation tube or the exterior of the urine tube.

14. The urethral catheter of claim 9 wherein the urine tube is fabricated from an elastomeric silicone material.

15. The urethral catheter of claim 9 wherein the inflatable balloon has a volume, said volume being generally less than or equal to 40 cc.

16. The urethral catheter of claim 9 wherein a collar encircles the urine tube and the inflation tube for being positioned in operative engagement with a person's pubic bone to thereby limit longitudinal movement of the urine tube and the inflation tube into the bladder.

17. In a urethral catheter for controlling a flow of urine from a bladder through a urethra of a person, said bladder having an interior, a neck region, and an orifice fluidly communicating with said urethra, said urethral catheter including a urine tube and an inflatable balloon connected to said urine tube, said urine tube having an exterior and said inflatable balloon having an interior, said urine tube extending through said interior of said inflatable balloon and fluidly communicating with said interior of said bladder, the improvement comprising:

the inflatable balloon having a generally non-spherical shape including an upper portion and a lower portion, said upper portion being generally larger than said lower portion, said lower portion of the inflatable balloon being sized so as to be received at least partially within the urethra generally proximate to the neck region and the orifice of the bladder to form a plug seal within the urethra when the inflatable balloon is inflated and said upper portion of the inflatable balloon is seated within the interior of the bladder contacting the bladder closely proximate to the neck region and the orifice, and whereby the plug seal formed by the inflatable balloon within the urethra prevents the flow of urine from within the bladder through the urethra on the exterior of the urine tube.

\* \* \* \* \*